United States Patent [19]
Gnägi

[11] Patent Number: 6,000,309
[45] Date of Patent: Dec. 14, 1999

[54] KNIFE FOR THE CRYO-ULTRAMICROTOMY

[75] Inventor: Helmut Gnägi, Ipsach, Switzerland

[73] Assignee: Anton Meyer & Co., AG, Switzerland

[21] Appl. No.: 09/069,860

[22] Filed: Apr. 30, 1998

[30] Foreign Application Priority Data

Jun. 23, 1997 [EP] European Pat. Off. .............. 97810397

[51] Int. Cl.$^6$ ....................................................... G01N 1/06
[52] U.S. Cl. ............................ 83/167; 83/915.5; 83/171; 83/856
[58] Field of Search ................................... 83/856, 915.5, 83/170, 171, 150, 167; 73/864.41; 62/320

[56] References Cited

U.S. PATENT DOCUMENTS

| | | | |
|---|---|---|---|
| 4,024,779 | 5/1977 | Taugner et al. | 83/915.5 X |
| 4,051,755 | 10/1977 | Raveed . | |
| 4,472,989 | 9/1984 | Endo | 83/856 X |
| 4,690,023 | 9/1987 | Berleth et al. | 83/856 X |
| 5,099,735 | 3/1992 | Kempe et al. | 83/856 X |
| 5,161,446 | 11/1992 | Holbl et al. | 83/915.5 X |
| 5,211,097 | 5/1993 | Grasselli | 83/698.11 |
| 5,535,654 | 7/1996 | Niesporek et al. | 83/915.5 X |
| 5,669,278 | 9/1997 | Metzner | 83/915.5 X |

FOREIGN PATENT DOCUMENTS

| | | |
|---|---|---|
| 0111291 | 6/1984 | European Pat. Off. . |
| 0167330 | 1/1986 | European Pat. Off. . |
| WO 9401751 | 1/1994 | WIPO . |

*Primary Examiner*—Rinaldi I. Rada
*Assistant Examiner*—Ana Luna
*Attorney, Agent, or Firm*—Rothwell, Figg, Ernst & Kurz

[57] ABSTRACT

The knife comprises a block (1) with a front face (3) in which a diamond blade (9) with a frontal surface (10) which is preferably coplanar with the front face (3), is held. The diamond blade (9) has a back surface (11) forming a cutting edge (12) together with the frontal surface (10). A plastic insert (14), preferably of epoxy resin, adjoins the back surface (11) spaced from the cutting edge (12). The insert (14) has a plane upper surface (15) whose plane intersects the frontal surface (10) at an angle of 80° to 87°, preferably about 84°. Thereby sectioning and section pick-up under a stereo microscope are facilitated.

6 Claims, 1 Drawing Sheet

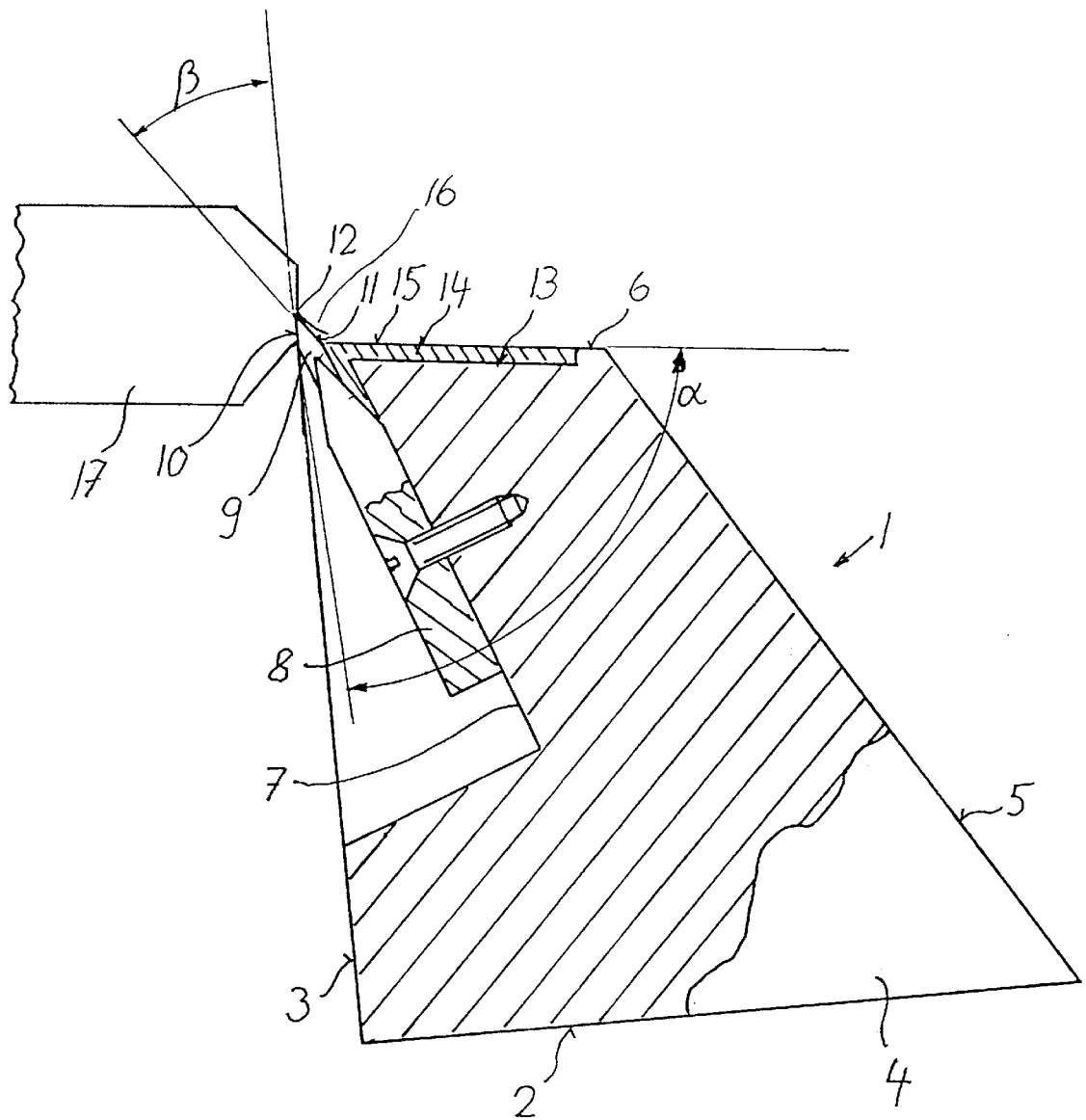

KNIFE FOR THE CRYO-ULTRAMICROTOMY

It is known to perform the cryo-ultramicrotomy with a knife containing a diamond cutting blade. One of the critical steps is the section collection from the diamond surface.

The problem of the present invention is to facilitate the collection of the sections. According to the present invention the knife comprises a block with a front face, in which a diamond blade with a frontal surface, which is preferably inclined at an angle of 4° to the front face, is held. The diamond blade has a back surface forming a cutting edge together with the frontal surface. A plastic insert, preferably of epoxy resin, adjoins the back surface spaced from the cutting edge. The insert has a plane upper surface whose plane intersects the frontal surface at an angle of 75° to 85°, preferably about 80°.

In operation the knife is mounted on a sled. The probe is movable in the vertical direction and advanced stepwise horizontally in steps according to the desired thickness of the sections to be cut, the range being between 10 nm and 10 μm. The cutting edge is horizontal. The frontal surface of the blade is set at a small clearance angle which is recommended at 10°. Therefore the upper surface of the insert is exactly horizontal. This greatly facilitates sectioning and section pick-up because these actions are performed under a stereo microscope with a magnification of 10 to 40 X. Because the upper surface of the insert is horizontal, no adjustment of the focus of the microscope is needed when the microscope is moved horizontally. The epoxy resin has suitable triboelectrical properties so that the sections easily slide over the upper surface and pick-up of the sections is facilitated. The knife is suitable for use in dry ultramicrotomy at low temperatures as well as for dry ultramicrotomy at ambient temperature.

An embodiment of the invention will be described below with reference to the drawing. The only figure shows a cross section through a knife.

A block 1 has a plane bottom face 2, a front face 3 which is perpendicular to face 2, two sidefaces 4 which are perpendicular to faces 2, 3, an inclined rear face 5 and a top face 6 the plane of which forms an angle of 84° with the front face 3. In a recess 7 in the front face 3 a holder 8 is mounted which holds a diamond blade 9. The blade 9 is sintered in the bronce holder 8 or vacuum braised in a tungsten carbide holder. The blade 9 has a plane frontal surface 10 and a back surface 11 forming together a cutting edge 12 which is parallel to the bottom face 2. The frontal surface 10 is inclined by 4° to the front face 3. The top face 6 has a further, flat recess 13 in which an insert 14 of epoxy resin with suitable triboelectrical properties is mounted. The insert 14 has a plane upper surface 15 which is coplanar with the top face 6. When the clearance angle of the frontal surface 10 with respect to a vertical plane is set at 10°, the surface 15 is exactly horizontal. The angle β of intersection of the frontal surface 10 and the back surface 11 is 25° to 45°, preferably about 35°. The figure shows the knife while cutting a section 16 from a probe 17.

What I claim is:

1. A knife for the cryo-ultramicrotomy, comprising a block (1) with a front face (3), in which a diamond blade (9) with a plane frontal surface (10) is held, the diamond blade (9) having a back surface (11) forming a cutting edge (12) together with the frontal surface (10), a plastic insert (14) adjoining the back surface (11) spaced from the cutting edge (12), said insert (14) having a plane upper surface (15) the plane of which intersecting the frontal surface (10) under an angle (α) of 75° to 85°.

2. The knife of claim 1, wherein the angle of intersection (α) is approximately 80°.

3. The knife of claim 1, wherein the insert (14) is of an epoxy resin.

4. The knife of claim 1, wherein the insert (14) has suitable triboelectrical properties.

5. The knife of claim 1, wherein the frontal surface (10) is inclined to the front face (3) by about 4°.

6. The knife of claim 1, wherein the intersecting angle (β) between the frontal surface (10) and the back surface (11) is 25° to 45°, preferably approximately 35°.

* * * * *